(12) United States Patent
Kojima et al.

(10) Patent No.: US 10,545,078 B2
(45) Date of Patent: Jan. 28, 2020

(54) STAINING AND STAINING PRE-TREATMENT METHODS AND DEVICES

(71) Applicant: ADSTEC CORPORATION, Chiba (JP)

(72) Inventors: Yuki Kojima, Kamagaya (JP); Kohei Sakashita, Koganei (JP)

(73) Assignee: Adstec Corporation, Funabashi, Chiba (JP)

( * ) Notice: Subject to any disclaimer, the term of this patent is extended or adjusted under 35 U.S.C. 154(b) by 259 days.

(21) Appl. No.: 15/390,097

(22) Filed: Dec. 23, 2016

(65) Prior Publication Data

US 2018/0113060 A1  Apr. 26, 2018

(30) Foreign Application Priority Data

Oct. 22, 2016 (JP) ................. 2016-207409

(51) Int. Cl.
*G01N 1/44* (2006.01)
*G01N 1/30* (2006.01)
*C12Q 1/68* (2018.01)
*G01N 1/31* (2006.01)

(52) U.S. Cl.
CPC ................. *G01N 1/44* (2013.01); *G01N 1/30* (2013.01); *G01N 1/31* (2013.01)

(58) Field of Classification Search
None
See application file for complete search history.

(56) References Cited

U.S. PATENT DOCUMENTS

2012/0301885 A1   11/2012  Tang

FOREIGN PATENT DOCUMENTS

| JP | 2013-520961 A | 6/2013 |
| WO | 2011106495 A1 | 9/2011 |

*Primary Examiner* — James Martinell
(74) *Attorney, Agent, or Firm* — Rosenberg, Klein & Lee (57) ABSTRACT

Staining nucleotides within chromosomes is an important technique used in cytogenetics to produce a visible karyotype by staining condensed chromosomes. Such techniques are useful, for example, in identifying genetic diseases through the photographic representation of the entire chromosome complement. Prior to the steps of selective dissolving and staining of nucleotides within the chromosomes an aging step is performed to increase the selective solubility between different nucleotides. Within the prior art this aging step is a time consuming process taking several days. Accordingly, it would be beneficial to provide a staining pretreatment method which can be performed in a short period of time.

20 Claims, 5 Drawing Sheets

STAINING AND STAINING PRE-TREATMENT METHODS AND DEVICES

CROSS-REFERENCE TO RELATED APPLICATIONS

This application claims the benefit of priority from Japanese Patent Application 2016-207409 filed Oct. 22, 2016 of which the entire contents are herein incorporated by reference.

FIELD OF THE INVENTION

This invention relates to chromosomal testing and more particularly to methods and devices for staining chromosomes together with a staining pretreatment method to be applied prior to the staining method.

BACKGROUND OF THE INVENTION

Chromosomal testing, also known as genetic testing, is a type of medical test that identifies changes in chromosomes, genes or proteins. Gene tests look for abnormalities in deoxyribonucleic acid (DNA) taken from a person's blood, body fluids or tissues. The tests can look for large mistakes such as a gene that has a section missing or added. Other tests look for small changes within the DNA. Other mistakes that can be found include genes that are too active, genes that are turned off, or those that are lost entirely. In order to differentiate the different nucleobases within DNA, namely adenine (A), thymine (T), guanine (G) and cytosine (C) (hereinafter, simply expressed by A, T, G and C) in the chromosomes, only a part of these four nucleotides is stained in the chromosomal testing.

Within the prior art, for example Tang et al. in WO/2011/106495 entitled "Cytogenic Analysis of Metaphase Chromosomes", the process of staining is time consuming process as result of a process step referred to as "aging." Prior to staining a chromosome, a portion of the nucleotides are dissolved in an enzyme in order that only those nucleotides which have not dissolved may be stained. More specifically, the process step of aging is performed in such a manner that only a part of nucleotides become sparingly soluble in the enzyme, and then the resultant material is immersed into the enzyme to enable "differential staining" for staining only A and T which become sparingly soluble in the enzyme. However, such aging has been the operation typically requiring a substantial period of time, typically days.

Accordingly, it would be beneficial to provide a staining pretreatment method according to which aging can be achieved in a short period of time thereby reducing the overall processing time for performing chromosome analysis.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to mitigate limitations within the prior art relating to chromosomal testing and more particularly to methods and devices for staining chromosomes together with a staining pretreatment method to be applied prior to the staining method.

In accordance with an embodiment of the invention there is provided a method comprising:
applying a staining pretreatment process to a sample containing chromosomes in order to selectively increase the solubility of a first nucleotide forming a first predetermined portion of each chromosome in a predetermined solvent with respect to a second nucleotide forming a second predetermined portion of each chromosome in the predetermined solvent; wherein
the pretreatment process comprises illuminating the sample containing the chromosome with ultraviolet optical radiation within the wavelength range 200 nm to 280 nm having a predetermined energy density for a predetermined period of time.

In accordance with an embodiment of the invention there is provided a system comprising:
an ultraviolet lamp for emitting ultraviolet radiation within the wavelength range 200 nm to 280 nm;
a holder for a substrate supporting a sample containing chromosomes to which a staining pretreatment process is to be applied prior to performing a staining process;
a motion system for positioning the holder and substrate into a first position with respect to the ultraviolet lamp to perform the staining pretreatment process and into at least a second position to perform a step within the staining process; wherein
the staining pretreatment process comprises illuminating the sample with the ultraviolet optical radiation at a predetermined energy density which is established in dependence upon at least the first position relative to the ultraviolet lamp and the power of the ultraviolet lamp for a predetermined period of time.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

The present invention is directed to chromosomal testing and more particularly to methods and devices for staining chromosomes together with a staining pretreatment method to be applied prior to the staining method.

The ensuing description provides representative embodiment(s) only, and is not intended to limit the scope, applicability or configuration of the disclosure. Rather, the ensuing description of the embodiment(s) will provide those skilled in the art with an enabling description for implementing an embodiment or embodiments of the invention. It being understood that various changes can be made in the function and arrangement of elements without departing from the spirit and scope as set forth in the appended claims. Accordingly, an embodiment is an example or implementation of the inventions and not the sole implementation. Various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention can also be implemented in a single embodiment or any combination of embodiments.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the inventions. The phraseology and terminology employed herein is not to be construed as limiting but is for descriptive purpose only. It is to be understood that where the claims or specification refer to "a" or "an" element, such reference is not to be construed as there being only one of that element. It is to be understood that where the specification states that a component feature, structure, or characteristic "may", "might", "can" or "could" be included, that particular component, feature, structure, or characteristic is not required to be included.

Reference to terms such as "left", "right", "top", "bottom", "front" and "back" are intended for use in respect to the orientation of the particular feature, structure, or element within the figures depicting embodiments of the invention. It would be evident that such directional terminology with respect to the actual use of a device has no specific meaning as the device can be employed in a multiplicity of orientations by the user or users. Reference to terms "including", "comprising", "consisting" and grammatical variants thereof do not preclude the addition of one or more components, features, steps, integers or groups thereof and that the terms are not to be construed as specifying components, features, steps or integers. Likewise, the phrase "consisting essentially of", and grammatical variants thereof, when used herein is not to be construed as excluding additional components, steps, features integers or groups thereof but rather that the additional features, integers, steps, components or groups thereof do not materially alter the basic and novel characteristics of the claimed composition, device or method. If the specification or claims refer to "an additional" element, that does not preclude there being more than one of the additional element.

A: Cross-Reference of Identifiers Employed

Within the patent specification below and in the Figures numeric identifiers are employed in association with identified elements that are described. The following table provides a simple cross-reference between such elements and their numeric identifiers.

| 100 | Staining system |
| 110 | Ultraviolet light source |
| 112 | Optical Filter |
| 120 | First liquid vessel for enzyme |
| 121 | Enzyme solution |
| 130 | Second liquid vessel for cleaning solution |
| 131 | Cleaning solution |
| 140 | Third liquid vessel for Giemsa solution |
| 141 | Giemsa solution |
| 150 | Fourth liquid vessel for Giemsa cleaning solution |
| 151 | Giemsa cleaning solution |
| 160 | Slide holder |
| 170 | Motion system |
| 180 | Glass slide |

B: Prior Art Ultraviolet Irradiation

As will be described and discussed below the inventors have established that low level UV irradiation of DNA may be employed to age the DNA such that specific nucleotides, e.g. G and C, can be selectively dissolved allowing the remaining nucleotides, e.g. A and T, to be stained and visualized. The inventors have established the UV irradiation as being within the range defined by $1,000 \ \mu Jcm^{-2} \leq Q \leq 30,000 \ \mu Jcm^{-2}$.

The inventors are aware that within the prior art of Tang DNA is exposed to higher energy UV irradiation with the aim of cross-linking bonds which is a distinctly different process with respect of the DNA than aging nucleotides within a chromosome to achieve different solubility rates for different nucleotides within an enzyme solution. Specifically, Tang describes such cross-linking being achieved at energies between 50 mJ (50,000 µJ) to about 500 mJ (500,000 µJ), preferably about 150 mJ (150,000 µJ) to 250 mJ (250,000 µJ), and most preferably at about 200 mJ (200,000 µJ). Accordingly, at the "most preferred" levels the teaching of Tang is to energy levels significantly different from that of the inventors. UV irradiation at these levels taught by Tang is unsuitably too much for the aging according to the present invention.

C: Exemplary Pre-Treatment and Staining System

Figure 1:
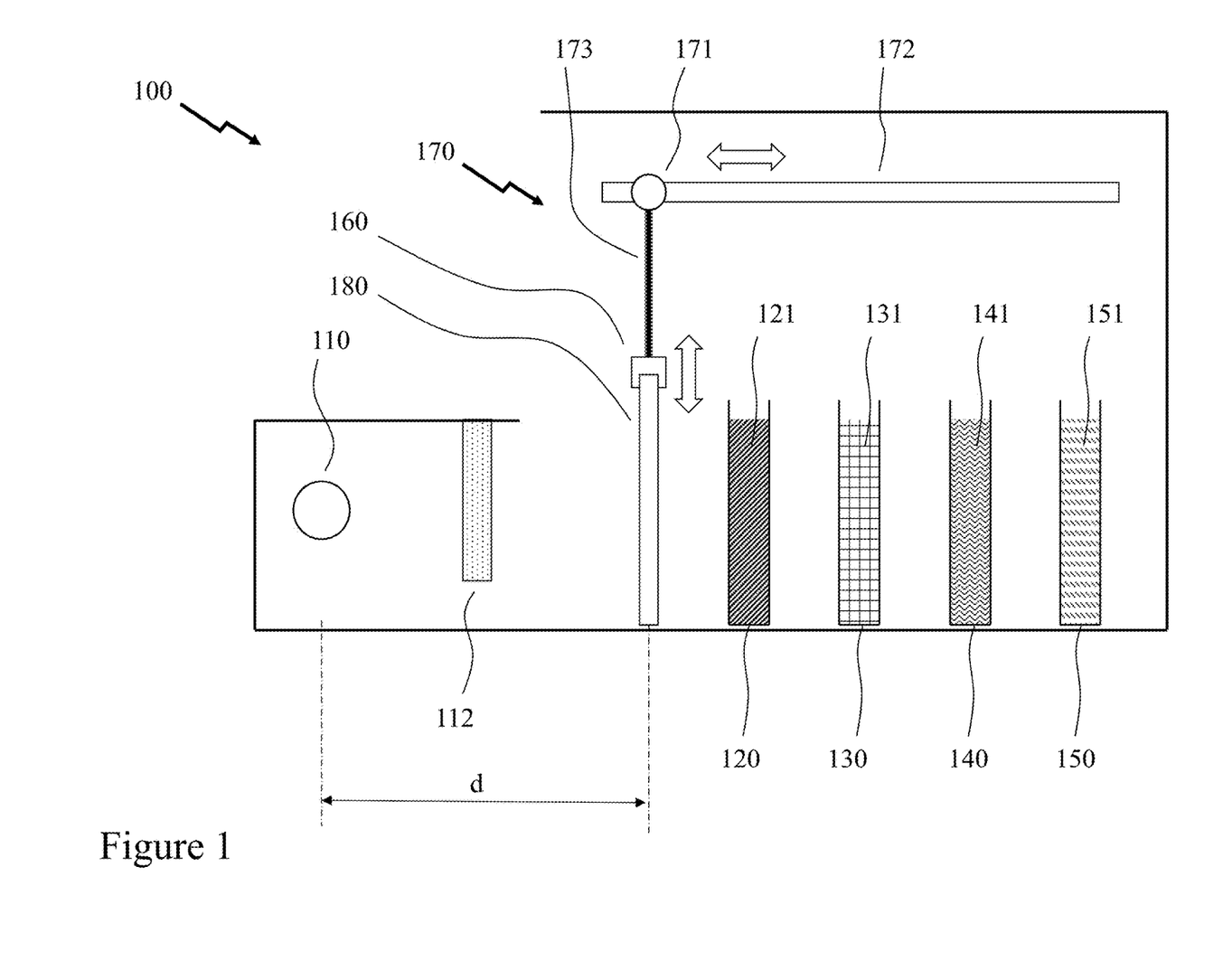
FIG. 1 depicts a schematic configuration of a staining device employing a staining method exploiting the staining pre-treatment method according to an embodiment of the invention.

Referring to FIG. 1 there is depicted a Staining System 100 according to an embodiment of the invention that provides for pre-treatment according to an embodiment of the invention and an overall chromosome staining process according to an embodiment of the invention. As depicted the Staining System 100 includes an ultraviolet (UV) light source 110 and an optical filter 112 in order to provide UV illumination within the Staining System 100. Also depicted within the Staining System 100 are a first liquid vessel 120 for an enzyme, a second liquid vessel 130 for a cleaning solution, a third liquid vessel 140 for a Giemsa solution, a fourth liquid vessel 140 for a Giemsa cleaning solution, a glass slide holder 160, and a motion system 170.

Operation of the Staining System 100 employs holding a glass slide 180 with the glass slide holder 160, filling the first liquid vessel 120 for the enzyme with an enzyme solution 121, filling the second liquid vessel 130 for the cleaning solution with a cleaning solution 131, filling the third liquid vessel 140 for the Giemsa solution with a Giemsa solution 141, and filling the fourth liquid vessel 140 for the Giemsa cleaning solution with a Giemsa cleaning solution 151. An exemplary process flow and schematic sequence of the Staining System 100 are described and depicted in respect of FIGS. 3 and 4 respectively.

The chromosomes to be stained may be cultured upon the glass slide 180 before the glass slide 180 is placed within the Staining System 100.

The UV light source 110 may be a lamp emitting ultraviolet radiation (light) at a predetermined intensity. Within embodiments of the invention the UV light source 110 may be a narrowband or wideband source having a wavelength range of 200 nm≤λ≤280 nm. The optical filter 112 is a neutral density filter or other filter for attenuating the UV light source 110 to a desired optical intensity.

The first liquid vessel 120 contains an enzyme and is a vessel for having the enzyme solution 121 filled and held therein. The enzyme solution 121 dissolves a nucleotide therein, in which a degree and a rate of dissolution are different depending on a state (degree of aging) of the nucleotide.

The second liquid vessel 130 contains a cleaner and is a vessel for having the cleaning solution 131 filled and held therein. The cleaning solution 131, for example, ethanol can be used to clean the enzyme contained in the enzyme solution 121.

The third liquid vessel 140 contains a Giemsa stain and is a vessel for having the Giemsa solution filled and held therein. The Giemsa solution 141 stains the chromosomes.

The fourth liquid vessel 140 contains a Giemsa cleaner and is a vessel for having the Giemsa cleaning solution 151 filled and held therein. The Giemsa cleaning solution 151 cleans the Giemsa solution 141. For example, water can be used as the Giemsa cleaning solution 151.

The slide holder 160 holds the glass slide 180 and is moved by the motion system 170 inside the Staining System 100 wherein the motion system 170 allows the slide holder to be raised/lowered and moved towards/away from the UV light source 110. As depicted the motion system 170 within the Staining System 100 comprises a cam 171 which moves along a support rod 172 in a horizontal direction, such as under the control of an electric motor, for example. Dropping down from the cam 171 is a chain 173 which moves the slide holder 160 in a vertical direction, such as under the control of another electric motor or the same electric motor if its drive is coupled/decoupled to provide motion of the cam 171 and slide holder 160. Chain 173 may be a chain or it may alternatively be wire, a cable, or another element.

Figure 2:
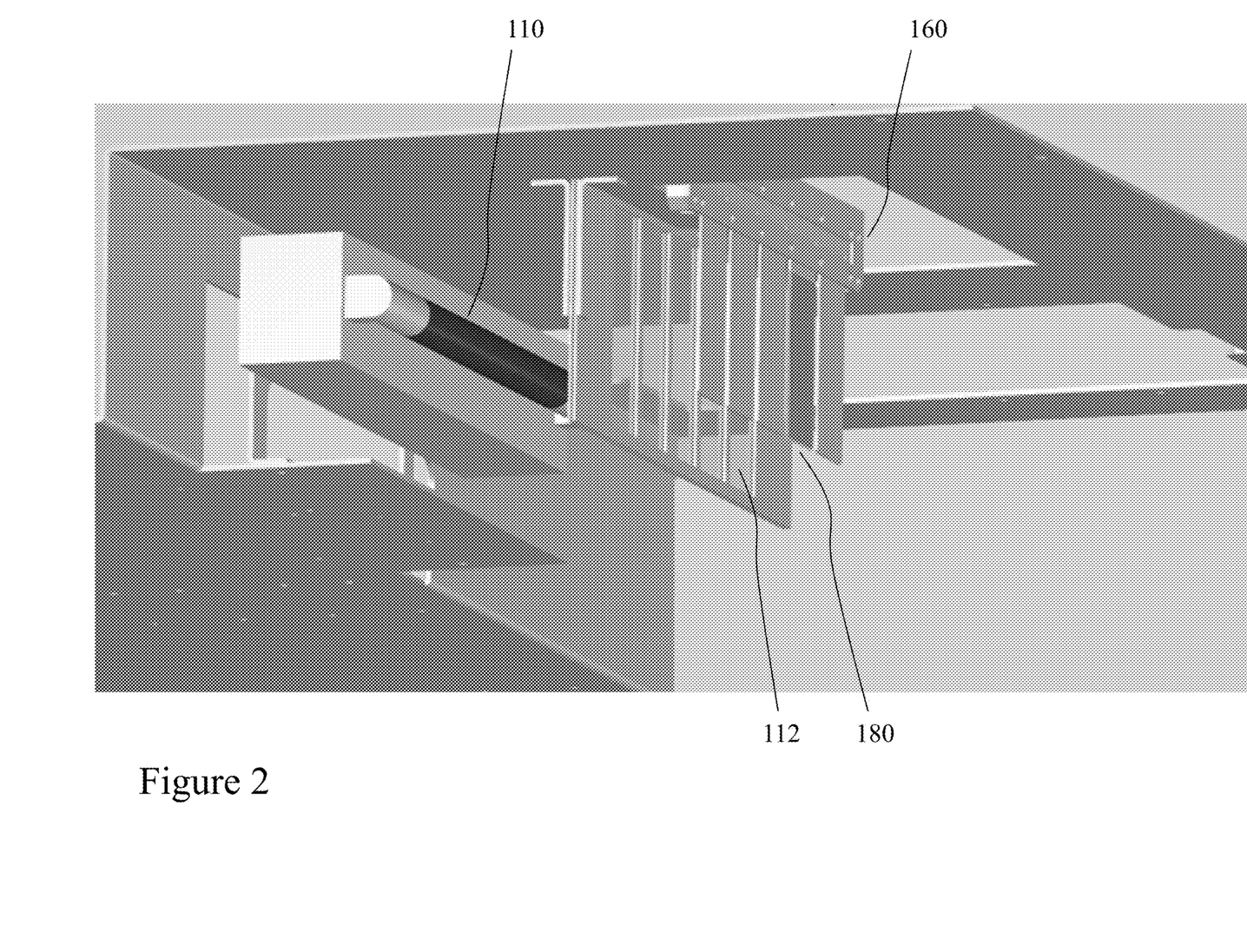
FIG. 2 depicts a partial configuration of the staining device depicted in FIG. 1 according to an embodiment of the invention.

Whilst an exemplary configuration is depicted in FIG. 1 the design and implementation of the motion system 170 is not limited thereto. Any configuration may be applied to provide the required functionality that the glass slide 180 held in a lower part of the slide holder 160 can be placed in a site to be irradiated with ultraviolet radiation from the UV light source 110, a site to be immersed into the liquid vessel 2 for the enzyme, a site to be immersed into the second liquid vessel 130 for the cleaning solution and a site to be immersed into the third liquid vessel 140 for the Giemsa solution, and then can move to other places after a predetermined period of time. As such a configuration, various configurations can be easily practiced. For example, chain 173 may be replaced with a screw drive whilst cam 171 is moved along support 172 by a linear translation stage. Whilst a configuration for the Staining System 100 is described and depicted with the first to fourth vessels 120, 130, 140 and 150 disposed linearly in one axis longitudinally disposed with increasing separation from the UV light source 110 it would be evident that other configurations may be employed without departing from the scope of the invention. For example, the first to fourth vessels 120, 130, 140 and 150 may be laterally disposed if the UV light source 110 is a compact source. As depicted in FIG. 2 multiple glass slides may be held upon a common slide holder 160 laterally in combination with linear UV light source 110.

The optical filter 112 is disposed between the UV light source 110 and the glass slide 180, with the slide holder 160 positioned in a predetermined location by the motion system 170. As described and discussed below the glass slide 180 is desirably irradiated with accumulated ultraviolet radiation at a UV power density between 50 $\mu Wcm^{-2}$ and 800 $\mu Wcm^{-2}$. It would be evident that with a UV light source 110 disposed approximately 8 cm (~3 inches) to 30 cm (~12 inches) the glass slide 180 is irradiated with ultraviolet radiation at the upper typical power density of 800 $\mu Wcm^{-2}$ with varying exposure times based upon UV light source 110 intensity and the separation between the UV light source 110 and glass slide 180. Whilst the intensity of ultraviolet radiation to be irradiated can be reduced by increasing the distance between the UV light source 110 and the glass slide 180 this leads to an increasing size of the Staining System 100 which may be unfavorable.

Alternatively, as depicted within FIG. 1 with Staining System 100 the distance, d, between the UV light source 110 and the glass slide 180 may be reduced for a given UV light source 110 by utilizing optical attenuation from an optical filter 112 to adjust the intensity of ultraviolet radiation to be irradiated to the range of 50 $\mu Wcm^{-2}$ to 800∪$Wcm^{-2}$. Accordingly, the intensity of the UV light source 110, the distance (d), and attenuation ratio, r, of the optical filter 112 (transmitted power/incident power) can be adjusted to achieve the desired irradiation power density and irradiation exposure time. Within many physical implementations such that the Staining System 100 occupies a small footprint when installed within a medical institution, the distance may be typically limited to a maximum distance d=30 cm. Moreover, in order to use common UV light sources 110 with d≤30 cm then a typical value for the attenuation ratio is r≤0.5 (i.e. attenuation ≤3 dB). Optionally, rather than a fixed filter a graded neutral density (ND) filter may be employed allowing the optical power density to be varied as the ND filter is adjusted between lower and/or higher values.

Now referring to FIG. 2 there is depicted a partial configuration of the staining device depicted in FIG. 1 according to an embodiment of the invention wherein a linear UV light source 110 is employed in conjunction with optical filters 112 and slides 180 attached to a common slide holder 160. Optionally, a single optical filter 112 may be employed. Optionally, for variable power management of the irradiation the optical filter 112 may be a variable ND filter that is raised/lowered to vary the attenuation applied to the UV light from the UV light source 110.

It would be evident that whilst FIG. 2 only depicts a partial configuration that the multiple slides 180 may be employed with either common first to fourth vessels 120, 130, 140 and 150 or with arrays of first to fourth vessels 120, 130, 140 and 150 for improved isolation between vessels and reduced cross-contamination risk from samples on different slides. It would be evident that multiple parallel "tracks" of staining pre-treatment and staining according to embodiments of the invention coupled with the reduced aging time would provide for enhanced efficiency in chromosomal testing.

Figure 3:
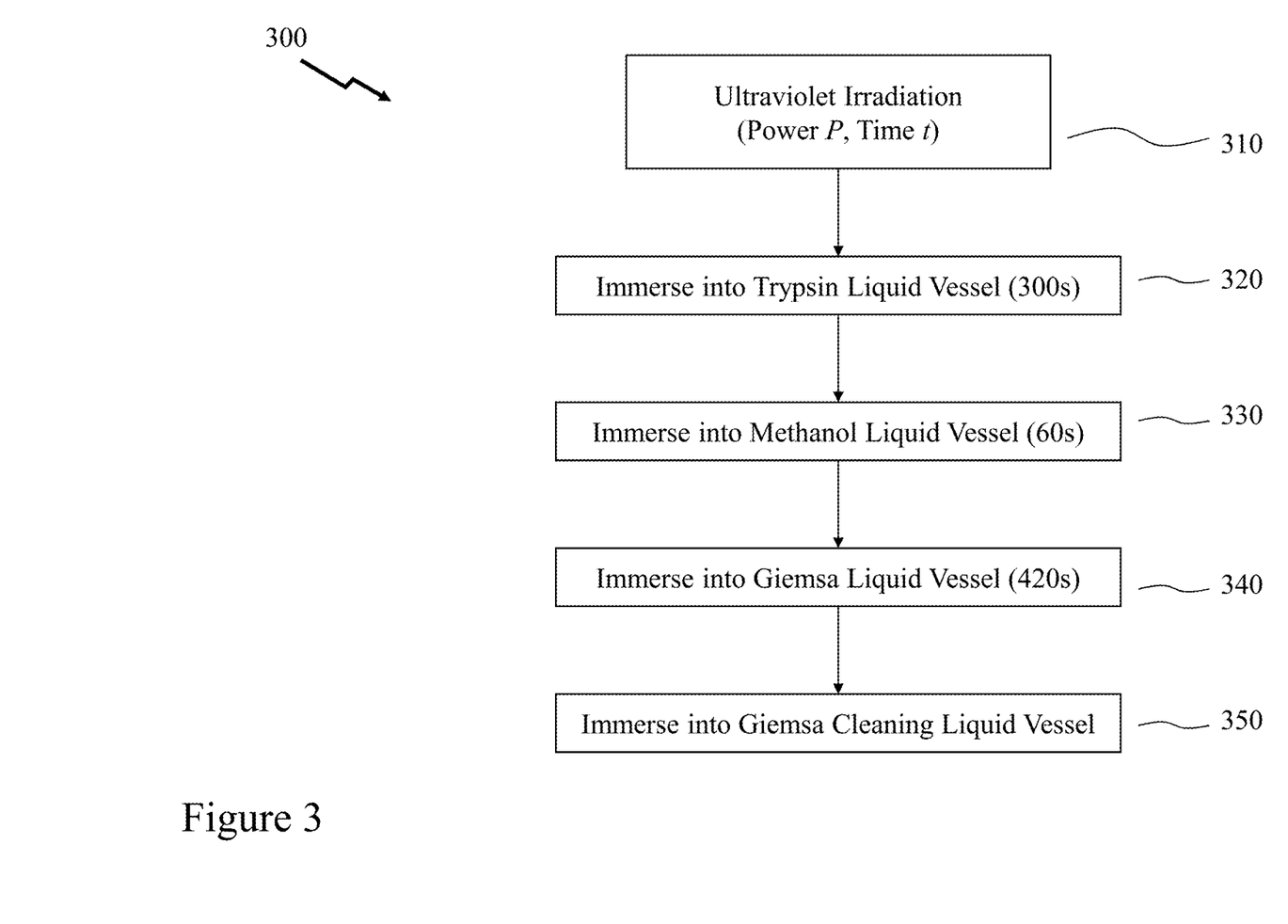
FIG. 3 depicts an exemplary process flow for a staining method exploiting the staining pre-treatment method according to an embodiment of the invention.

FIG. 3 depicts an exemplary process flow 300 for a staining method exploiting the staining pre-treatment method according to an embodiment of the invention. As depicted the process begins with an Ultraviolet Irradiation step 310 which provides for the reduced aging time compared with the prior art. The ultraviolet irradiation being undertaken at a power P for a duration t. Once the sample has been aged then it proceeds through the following steps:

Enzyme treatment step 320;
Cleaning step 330;
Giemsa stain step 340; and
Giemsa cleaning step 350.

It would be evident to one skilled in the art that the cleaning step 330 and the Giemsa cleaning step 350 are not always necessary, and may be omitted. Further, other staining methods other than Giemsa staining may be employed without departing from the scope of the invention and some of these may require additional processing steps and/or removal of cleaning steps.

Prior to the execution of the staining process 300, the chromosomes are either cultured in-situ upon the glass slide 180 or are cultured and transferred to the glass slide 180. Whilst within embodiments of the invention are described with respect to a glass slide 180 for mechanically supporting the cultured chromosomes during the staining pre-treatment according to an embodiment of the invention and the subsequent staining process it would be evident that the traditional soda lime glass slide or borosilicate glass slide is a substrate to support the biological sample and/or culture containing the chromosomes and may be replaced with other materials providing the required mechanical support, inert substrate, and either an optically flat or patterned surface. Such materials may include, but not be limited to, other glasses, fused quartz, silicon, silicon-on-insulator, plastic, metal, and an alloy.

The aging step 310 is provided for by the motion system 170 to place the slide holder 160 in the site shown in FIG. 1 and in first configuration 410 in FIG. 4 to irradiate the glass slide 180 with UV radiation, in which an irradiation time t and UV light source power P determine the degree of aging, as described subsequently below.

The enzyme treatment step 320 is provided for exposing the chromosomes after aging to the enzyme. The motion system 170 places the slide holder 160 in a site shown in second configuration 420 in FIG. 4 to immerse the glass slide 180 into the enzyme solution 121. For the enzyme solution 121, a trypsin solution may be generally used. The trypsin solution is used also in the present exemplary embodiments. However, it would be evident to one of skill in the art that other enzyme solutions 121 may be employed.

The nucleotide is dissolved in the enzyme (trypsin), but as a result of the aging, the A and T nucleotides react slower with the enzyme. Accordingly, when the chromosomes are exposed to the enzyme (trypsin) for a predetermined duration, for example 300 seconds, the G and C nucleotides are dissolved in the enzyme (trypsin), but the A and T nucleotides are not appreciably dissolved therein such that these remain for staining.

The duration of "300 seconds" may be appropriately increased or decreased to 150 seconds, 450 seconds or the like as an engineering expedient, although such deviations would yield a significant difference between dissolution of the A and T nucleotides and dissolution of the G and C nucleotides. Essentially, at very short durations of exposure the G and C nucleotides are not dissolved significantly, whereas at longer exposure times the A and T nucleotides are also dissolved together with the G and C nucleotides.

The cleaning process 330 is provided in order to remove enzyme solution (trypsin solution) 121 remaining on the glass slide 180 to stop action of the enzyme (trypsin). As the cleaning solution 131, ethanol is generally used. Ethanol is used also in the present exemplary embodiments. Cleaning is, typically, sufficiently made in 60 seconds. In performing this step, the motion system 170 places the slide holder 160 in a site shown in third configuration 430 in FIG. 4 to immerse the glass slide 180 into the cleaning solution 131.

In the embodiments of the invention exploiting Giemsa solution 141 for the staining step then the standard "recipe" for Giesma solution 141 includes methanol, which is of itself a solvent for the enzyme solution 121. Accordingly, in this scenario and others where a solvent is part of the staining solution recipe than the enzyme solution is cleaned by the staining solution, e.g. Giemsa solution 141, and the cleaning process 330 may in such instances be omitted. In performing this step, the motion system 170 places the slide holder 160 in a site shown in fourth configuration 440 in FIG. 4 to immerse the glass slide 180 into the Giesma solution 141.

The Giemsa stain step 340 is provided for staining the nucleotide. Staining is, typically, sufficiently achieved in 420 seconds. As the G and C nucleotides are dissolved during the enzyme treatment step 320 then these are not appreciably stained, whilst the A and T nucleotides which are not dissolved therein are darkly stained. Accordingly, the chromosomes in which an amount of G and C each is large (or small) are identified by observing the stained chromosomes wherein dark stains represent A/T nucleotides and light regions represent G/C nucleotides. In this manner chromosomal testing can be conducted.

The Giemsa cleaning step 350 is provided for removing the Giemsa solution 141 remaining on the glass slide 180 to complete staining. As noted supra this step may in some embodiments of the invention be omitted. In performing this step, the motion system 170 places the slide holder 160 in a site shown in fifth configuration 450 in FIG. 4 to immerse the glass slide 180 into the Giesma cleaning solution 151, typically methanol although in other embodiments of the invention other suitable cleaning solutions may be employed. Methanol is used in the present exemplary embodiments.

Figure 4:
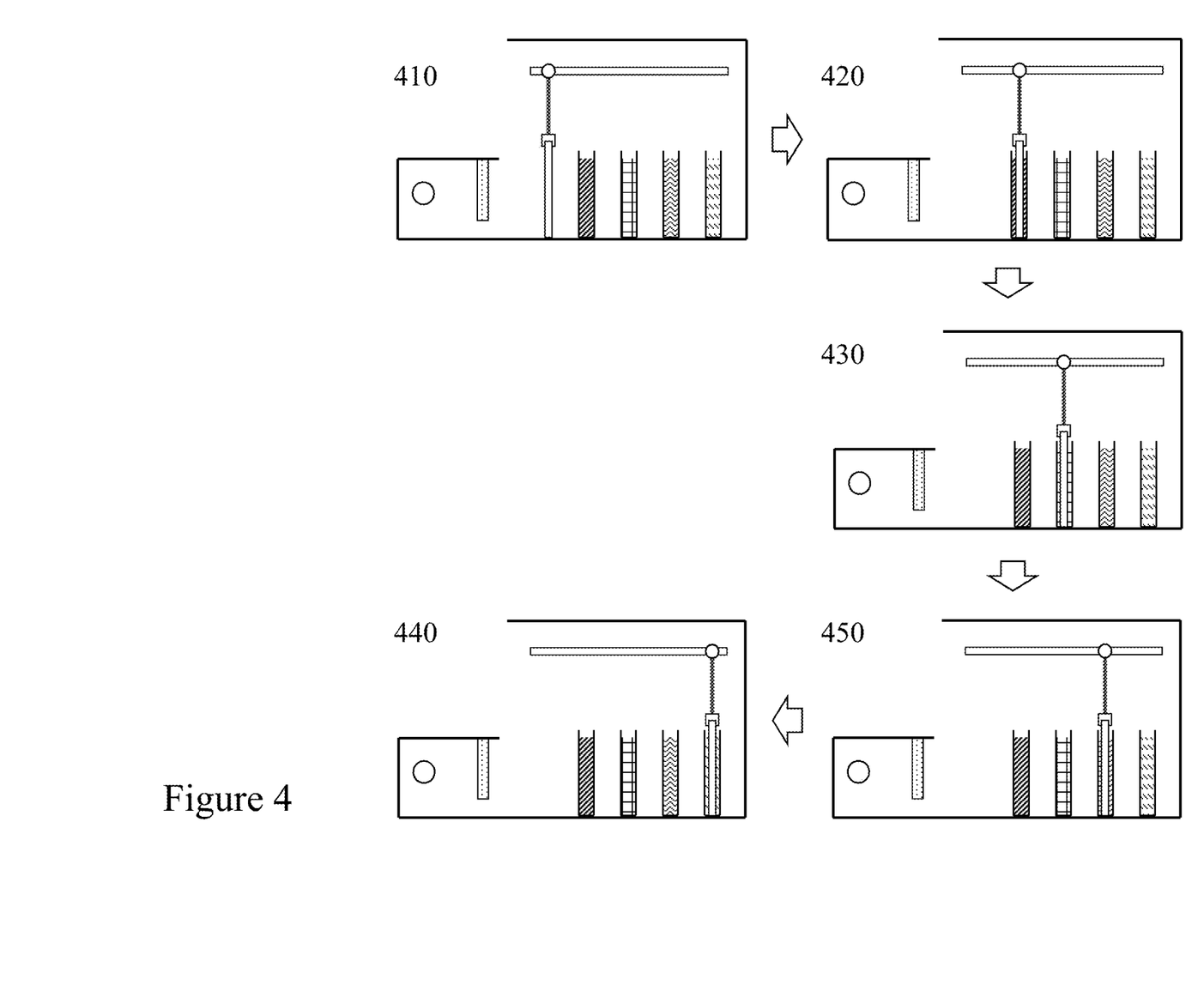
FIG. 4 depicts an exemplary sequence for performing the process described in FIG. 3 with a staining device as depicted in FIG. 1 according to an embodiment of the invention.

As noted supra FIG. 4 depicts an exemplary sequence for performing the process described in FIG. 3 with a staining device as depicted in FIG. 1 according to an embodiment of the invention in first to fifth configurations 410 to 450 respectively.

The motion system 170 first arranges, as shown in first configuration 410 in FIG. 4 (similar to FIG. 1), the glass slide 180 in a site to be irradiated with UV radiation. The motion system 170 only needs to move the slide holder 160 to an upper part in the figure by a chain 73 to move a cam 71 above the site to be irradiated with UV radiation, and then loosen the chain 73 to move the slide holder 160 to a lower part in the figure (site in FIG. 4). Thus, the site of the glass slide 180 can be adjusted to the site for each step of the staining procedures by adjusting the site in the horizontal direction in the figure in the upper part of the figure, and moving the slide holder 160 to the lower part in the figure therefrom. In a state in first configuration 410 in FIG. 4, the aging process 310 is executed. Then, the motion system 170 executes the enzyme treatment step 320 after a time t as a state of second configuration 420 in FIG. 4, the cleaning step 330 after 300 seconds as a state of third configuration 430 in FIG. 4, the Giemsa stain step 340 after 60 seconds as a state of fourth configuration 440 in FIG. 4, and the Giemsa cleaning step 350 after 420 seconds as a state of fifth configuration 450 in FIG. 4, and then moves the glass slide 180 upward to complete staining.

C: Examination of Aging Step Duration

In the following, the time t in the aging step 310 is discussed. The inventors have found that UV radiation having the wavelength of 200 nm A 280 nm when irradiated at energy intensities, $E_\rho$, of 1,000 $\mu Jcm^{-2} \leq E_\rho \leq 30,000$ $\mu Jcm^{-2}$ results in reducing the reaction of G and C nucleotides to the enzyme (trypsin), and not appreciably reducing a reaction of the A and T nucleotides to the enzyme (trypsin). The reaction of G and C nucleotides to the enzyme (trypsin) is not appreciably reduced by irradiation at $E_\rho \leq 1,000$ $\mu Jcm^{-2}$ whilst the reaction of A and T nucleotides to the enzyme (trypsin) is eventually reduced by irradiation at intensity $E_\rho > 30,000$ $\mu Jcm^{-2}$. More specifically, in order to perform differential staining between "A and T," nucleotides and "G and C" nucleotides, namely to stain A and T nucleotides further (darker) than G and C nucleotides), an irradiation quantity is required to be adjusted to 1,000 $\mu Jcm^{-2} \le E_\rho \le 30,000$ $\mu Jcm^{-2}$.

Within the range 1,000 $\mu Jcm^{-2} \le E_\rho \le 30,000$ $\mu Jcm^{-2}$ an effect caused by decrease or increase in the irradiation quantity is discussed. When the quantity is close to 1,000 $\mu Jcm^{-2}$, the reaction of A and T to the enzyme (trypsin) whilst occurring is such that the staining as a whole is light. When the quantity is close to 30,000 $\mu Jcm^{-2}$, the reaction of A and T nucleotides to the enzyme (trypsin) is reduced into dark staining as a whole. However, the reaction of G and C nucleotides to the enzyme (trypsin) is also further increased, and therefore G and C nucleotides are also stained further darkly.

A view on which levels of staining is preferable varies depending on preference of medical personnel conducting the chromosomal testing, a purpose thereof, and other conditions. Among the conditions, the irradiation quantity of 5,000 $\mu Jcm^{-2} \le E_\rho \le 8,000$ $\mu Jcm^{-2}$ results in strong contrast between "A and T," and "G and C" after staining.

If the irradiation intensity of UV light source 110 at a location of away from it is taken as I ($\mu Wcm^{-2}$) at a distance of 1 cm and an attenuation coefficient of the optical filter 112 is taken as r, then the irradiation quantity q ($\mu Jcm^{-2}$) for the sample at a distance, w (cm), away is determined by Equation (1) below for a standard radiative emitter without collimating optics etc.

$$q = \frac{I \times r \times t}{w^2} \quad (1)$$

Values of I, r and w herein are determined by a structure of the Staining System 100, although as noted supra r may be a variable through the user of a variable density filter or swapping different filters in/out. Accordingly, if a target irradiation quantity is taken as Q, an irradiation time t is determined so as to satisfy Equation (2) below.

$$t = \frac{Q \times w^2}{I \times r} \quad (2)$$

Accordingly, if we set Q=8,000 $\mu Jcm^{-2}$, w=30 cm. i (1 cm)=1 $Wcm^{-2}$, and r=0.25 then we find that t=28.8 s. Accordingly, sufficient aging is obtained by UV irradiation for about 30 seconds rather than days.

Here, a value of Q/t indicating the irradiation intensity to the glass slide 18 or a value of (I×r)/w$^2$ is preferably adjusted to between 50 $\mu Wcm^{-2} \le (I \times r)/w^2 \le 800$ $\mu Wcm^{-2}$. In the example above (I×r)/w$^2$=278 $\mu Wcm^{-2}$. As the value of Q/t increases, aging can be achieved in a shorter period of time, but the irradiation quantity becomes unstable by fluctuations in movement of the motion system and others. Further with the timing of the subsequent steps the aging is now no longer the rate limiting step. It is typically preferable not to 800 $\mu Wcm^{-2}$. Moreover, when the quantity is adjusted to satisfy the design equations then the inventors typically define Q=30,000 $\mu Jcm^{-2}$ and t≤600 s or Q/t≤50 $\mu Jcm^{-2}$ as being preferably satisfied.

Using typically established boundary conditions for the expressions above of 50 $\mu Jcm^{-2} \le Q/t \le 400$ $\mu Jcm^{-2}$ and 1,000 $\mu Jcm^{-2} \le Q \le 30,000$ $\mu Jcm^{-2}$ then t is defined within a range 2.5 s≤t≤60 s such that aging may be the matter of a few seconds or a few minutes.

Figure 5:
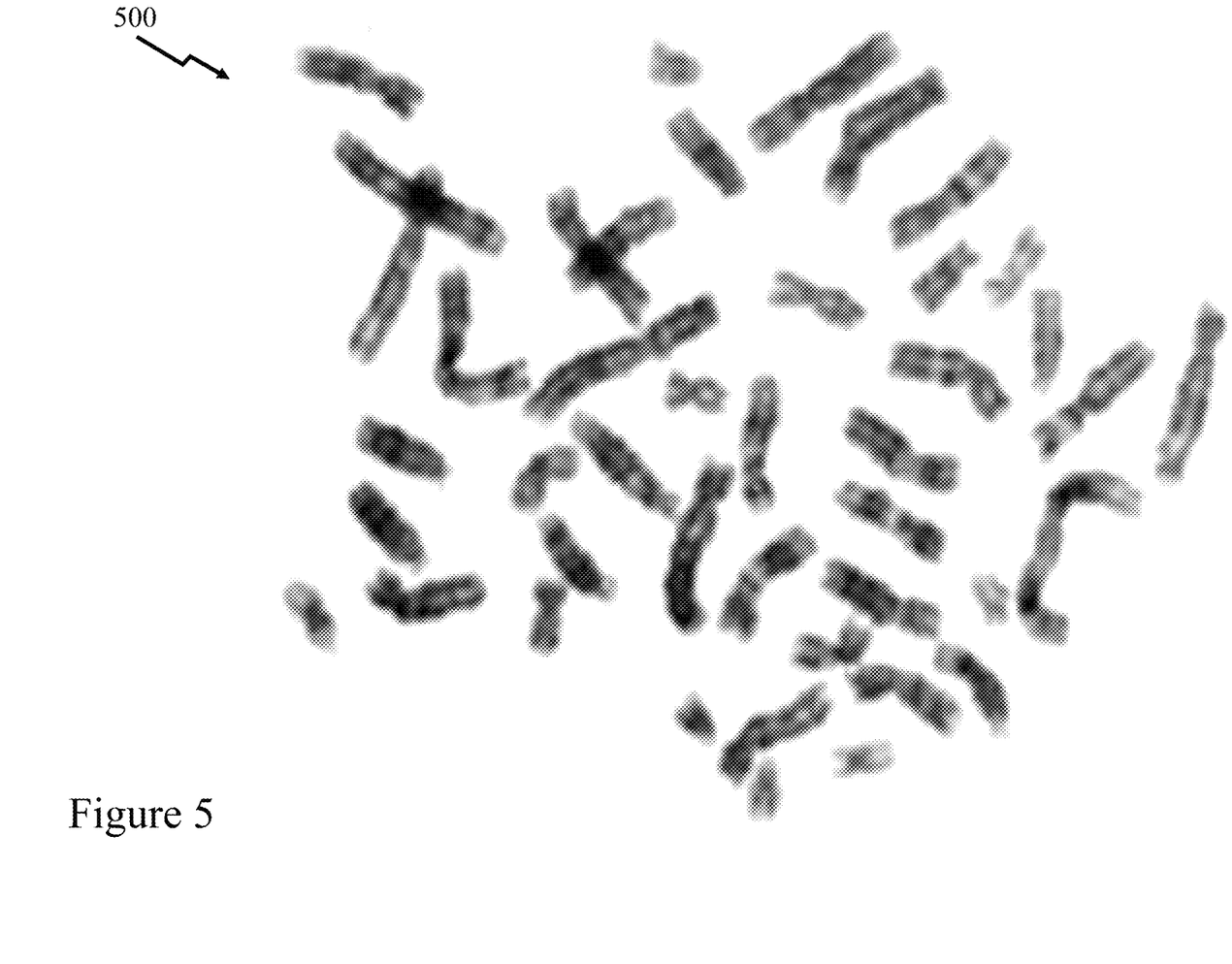
FIG. 5 depicts an optical micrograph of stained chromosomes after processing according to an embodiment of the invention.

Now referring to FIG. 5 there is depicted an optical micrograph 500 of stained chromosomes after processing according to an embodiment of the invention described supra wherein the amount of A and T nucleotides can be easily recognized visually.

As described in detail above, according to the staining pretreatment method in the present Example, aging in a short period of time can be achieved. According to the staining method in the present Example, staining can be achieved in a short period of time. According to the staining device in the present Example, staining in a short period of time can be automatically achieved.

Accordingly, a first embodiment of the invention comprises a staining pretreatment method of the present invention is provided with a staining pretreatment method according wherein aging for staining chromosomes is performed, and the chromosomes are irradiated with ultraviolet radiation having a wavelength of 200 nm to 280 nm for a period of time of 600 seconds or less.

Accordingly, a second embodiment of the invention comprises aging can be achieved in a short period of time. The present applicants have found that aging can be achieved by irradiating the chromosomes with ultraviolet radiation having the wavelength of 200 to 280 nm at 1,000 $\mu Jcm^{-2}$ to 30,000 $\mu Jcm^{-2}$.

Accordingly, a third embodiment of the invention comprises a staining pretreatment method of the present invention is provided with a total quantity of energy of the ultraviolet radiation to be irradiated is 1,000 $\mu Jcm^{-2}$ to 30,000 $\mu Jcm^{-2}$.

Accordingly, a fourth embodiment of the invention comprises ultraviolet radiation in a quantity suitable for aging is irradiated.

Accordingly, a fifth embodiment of the invention comprises a staining pretreatment method of the present invention is provided with the total quantity of energy of the ultraviolet radiation to be irradiated is 5,000 $\mu Jcm^{-2}$ to 8,000 $\mu Jcm^{-2}$.

Accordingly, a sixth embodiment of the invention comprises applying ultraviolet radiation in a quantity suitable for aging is irradiated onto samples and may be adjusted depending on density of an image obtained after differential staining and/or preference of testing personnel or a clinical laboratory technologist related to contrast Accordingly, a seventh embodiment of the invention comprises a staining pretreatment method of the present invention is provided with intensity of ultraviolet radiation to be irradiated is 50 $\mu Wcm^{-2}$ to 800 $\mu Jcm^{-2}$.

Accordingly, an eighth embodiment of the invention comprises irradiation by 1,000 $\mu Jcm^{-2}$ to 30,000 $\mu Jcm^{-2}$ is achieved within an irradiation time from 1.25 to 600 seconds. Aging can be achieved in a short period of time of 600 seconds or less. Moreover, although the chromosomes can be theoretically irradiated, for example, with a required quantity of ultraviolet having high intensity in about 0.1 second, fluctuations of the quantity to be irradiated may be caused depending on accuracy of the motion system or the like as describing later. Irradiation in a period of time of 1.25 seconds or more is preferably applied.

Accordingly, a ninth embodiment of the invention comprises a staining method of the present invention comprises staining chromosomes for chromosomal testing, and the method comprises an aging step for executing the staining pretreatment prior to an enzyme treatment step for exposing the chromosomes to an enzyme and a Giemsa stain step for executing Giemsa stain.

Accordingly, a tenth embodiment of the invention comprises a staining method comprises applying the staining pretreatment method of the present invention is provided.

Accordingly, an eleventh embodiment of the invention comprises a staining method is provided with the enzyme is trypsin.

Accordingly, a twelfth embodiment of the invention comprises a staining device of the present invention is provided with a staining device for executing a staining method, and having an ultraviolet light source for emitting ultraviolet radiation having a wavelength of 200 to 280 nm, a slide holder for holding a glass slide, a liquid vessel for an enzyme, and a liquid vessel for Giemsa solution.

Accordingly, a thirteenth embodiment of the invention comprises a staining device used for executing the staining method of the present invention is provided. Differential staining can be achieved by placing the glass slide under irradiation with ultraviolet radiation by controlling the slide holder for holding glass slide, immersing the glass slide into the liquid vessel for the enzyme, and immersing the resultant material into the liquid vessel for the Giemsa solution. In addition, a temperature regulating function is preferably provided for the liquid vessel for the enzyme to control a reaction of the enzyme.

Accordingly, a fourteenth embodiment of the invention comprises a staining device is provided with having a filter for attenuating ultraviolet radiation between a place in which the glass slide to be held by the slide holder is disposed, and the ultraviolet lamp.

Accordingly, a fifteenth embodiment of the invention comprises varying a quantity of ultraviolet irradiation to the glass slide by a filter. In view of an objective of the present invention comprises the ultraviolet lamp widely used emits strong ultraviolet radiation. Although the problem may be dissolved if a distance between the ultraviolet lamp and the glass slide is increased, a size of the staining device is increased. Ultraviolet radiation is preferably attenuated by the filter to prevent an increase of the size of the staining device.

Accordingly, a sixteenth embodiment of the invention comprises a staining device of the present invention is provided with the filter that attenuates ultraviolet radiation at a ratio of 0.5 or less.

Accordingly, a seventeenth embodiment of the invention comprises attenuation of ultraviolet radiation for reducing the size of the staining device is achieved.

Accordingly, an eighteenth embodiment of the invention comprises a staining device of the present invention is provided with which the distance between the place in which the glass slide to be held by the slide holder is disposed, and the ultraviolet lamp is 30 cm or less.

Accordingly, a nineteenth embodiment of the invention comprises the staining device having a reduced size is provided as a result of attenuating ultraviolet radiation by the filter.

Accordingly, a twentieth embodiment of the invention comprises a staining device of the present invention is provided with having a motion system for moving the slide holder, in which the motion system moves the slide holder in such a manner that the glass slide to be held by the slide holder moves in the order of a place to be irradiated with ultraviolet radiation, a place to be immersed into the liquid vessel for the enzyme and a place to be immersed into the liquid vessel for the Giemsa solution.

Accordingly, a twenty first embodiment of the invention comprises a staining device for automatically staining the chromosomes by the motion system is provided.

Beneficially, a staining pretreatment method of the present invention allows aging can be achieved in a short period of time.

Beneficially, a staining method of the present invention comprises a period of time of aging is shortened, and staining can be achieved in a short period of time.

Beneficially, a staining device of the present invention comprises staining in a short period of time can be automatically achieved by utilizing the staining pretreatment method of the present invention.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method comprising:
applying a pretreatment process to a sample containing chromosomes to increase enzymatic dissolution of a first nucleotide forming a first predetermined portion of each chromosome in a predetermined solution with respect to the enzymatic degradation of a second nucleotide forming a second predetermined portion of each chromosome in the predetermined solution; wherein
the pretreatment process comprises illuminating the sample containing the chromosomes with ultraviolet optical radiation within the wavelength range 200 nm to 280 nm having a predetermined energy density for a predetermined period of time.

2. The method according to claim 1, wherein
at least one of:
the predetermined period of time is less than 600 seconds;
the ultraviolet optical radiation irradiates the sample at between 1,000 microjoules and 30,000 microjoules per square centimeter;
the ultraviolet optical radiation irradiates the sample at between 5,000 microjoules and 8,000 microjoules per square centimeter; and
the ultraviolet optical radiation irradiating the sample has an intensity between 50 microwatts and 800 microwatts per square centimeter.

3. The method according to claim 1, further comprising performing an enzyme treatment step comprising at least the predetermined solution; and
performing a Giemsa stain step.

4. The method according to claim 1, further comprising performing an enzyme treatment step comprising at least trypsin.

5. The method according to claim 1, wherein
the first nucleotide is G or C; and
the second nucleotide is A or T.

6. A method for analyzing chromosomes comprising:
pretreating a sample of chromosomes with ultraviolet radiation at between 1,000 and 30,000 microjoules per square centimeter to increase enzymatic degradation of a first group of nucleotides in the sample of chromosomes by an enzyme relative to the enzymatic degradation of a second group of nucleotides in the sample of chromosomes by the enzyme.

7. The method of claim 6, wherein
at least one of:
the ultraviolet radiation has a wavelength between 200 nm and 280 nm; and
the step of pretreating with ultraviolet radiation is performed with a duration of between 1.25 and 600 seconds.

8. The method of claim 6, wherein
the enzyme is trypsin.

9. The method of claim 6, further comprising the step of treating the pretreated chromosomes with the enzyme.

10. The method of claim 9, wherein the enzyme is trypsin.

11. The method of claim 9, further comprising
staining the enzyme treated chromosomes with stain.

12. The method of claim 11, wherein the stain is Giemsa.

13. The method of claim 12, further comprising
at least one of:
one or more first washing steps between the pretreating step and enzyme treatment step; and
one or more second washing steps between the enzyme treatment step and the staining step.

14. The method of claim 6, further comprising
culturing the chromosomes in situ.

15. The method of claim 6, further comprising
culturing the chromosomes;
harvesting the chromosomes; and
applying the cultured and harvested chromosomes to a glass slide.

16. A method comprising:
applying a pretreatment process to a sample containing chromosomes, said process comprising:
illuminating the sample containing the chromosomes with ultraviolet optical radiation within the wavelength range 200 nm to 280 nm having a predetermined energy density for a predetermined period of time; wherein
said step of illuminating the sample results in an increased enzymatic degradation of G and C nucleotides in the sample upon exposure to an enzyme compared to enzymatic degradation of A and T nucleotides in the sample upon exposure to the enzyme.

17. The method according to claim 16, wherein
at least one of:
the predetermined period of time is less than 600 seconds;
the ultraviolet optical radiation irradiates the sample at between 1,000 microjoules and 30,000 microjoules per square centimeter;
the ultraviolet optical radiation irradiates the sample at between 5,000 microjoules and 8,000 microjoules per square centimeter; and
the ultraviolet optical radiation irradiating the sample has an intensity between 50 microwatts and 800 microwatts per square centimeter.

18. The method of claim 16, wherein
at least one of:
the enzyme is trypsin; and
the process further comprises treating the pretreated chromosomes with the enzyme.

19. The method of claim 16, further comprising
staining the pretreated and enzyme treated chromosomes with a stain.

20. The method of claim 16, further comprising
performing a solubilising process comprising exposing the pretreated sample to the enzyme;
performing a staining process after the solubilising process; and
at least one of:
one or more first washing steps between the pretreating process and solubilising process; and
one or more second washing steps between the solubilising process and the staining process.

* * * * *